(12) United States Patent
Gagneur et al.

(10) Patent No.: US 7,634,827 B2
(45) Date of Patent: Dec. 22, 2009

(54) SUPPORT DEVICE AND MAGNETIC RESONANCE DEVICE HAVING A SUPPORT DEVICE

(75) Inventors: Klaus Gagneur, Baiersdorf (DE); Ludwig Kreischer, Dormitz (DE); Tino Völker, Saalfeld (DE); Herbert Weiler, Alling (DE)

(73) Assignee: Siemens Aktiengesellschaft, Munich (DE)

( * ) Notice: Subject to any disclaimer, the term of this patent is extended or adjusted under 35 U.S.C. 154(b) by 962 days.

(21) Appl. No.: 11/001,603

(22) Filed: Dec. 1, 2004

(65) Prior Publication Data

US 2005/0204472 A1 Sep. 22, 2005

(30) Foreign Application Priority Data

Dec. 4, 2003 (DE) ................. 103 57 067
Oct. 27, 2004 (DE) ............ 10 2004 052 265

(51) Int. Cl.
*A61B 6/04* (2006.01)
(52) U.S. Cl. .............. 5/601; 5/81.1 HS; 378/209
(58) Field of Classification Search ........ 5/601, 5/600, 81.1 HS, 81.1 R, 81.1 C; 378/209
See application file for complete search history.

(56) References Cited

U.S. PATENT DOCUMENTS

| 3,428,307 | A | * | 2/1969 | Hunter et al. ............... 5/601 |
| 3,588,500 | A | * | 6/1971 | Koerner ..................... 5/601 |
| 4,475,072 | A | * | 10/1984 | Schwehr et al. ........... 318/602 |
| 4,568,071 | A | * | 2/1986 | Rice ........................... 5/601 |
| 4,773,637 | A | * | 9/1988 | Jarin ........................... 5/600 |
| 5,210,893 | A | * | 5/1993 | Uosaki et al. ............... 5/601 |
| 5,619,763 | A | * | 4/1997 | Randolph et al. .......... 5/601 |
| 5,960,054 | A | * | 9/1999 | Freeman et al. ........... 378/4 |
| 6,615,428 | B1 | * | 9/2003 | Pattee ......................... 5/601 |
| 6,955,464 | B1 | * | 10/2005 | Tybinkowski et al. ..... 378/209 |
| 7,065,813 | B2 | * | 6/2006 | Hoth et al. ................. 5/601 |
| 7,167,739 | B2 | * | 1/2007 | Van De Rijdt et al. ..... 600/415 |
| 7,430,772 | B2 | * | 10/2008 | Van Es ....................... 5/601 |
| 7,437,785 | B2 | * | 10/2008 | Farooqui .................... 5/601 |
| 2004/0255382 | A1 | * | 12/2004 | Van De Rijdt et al. ..... 5/601 |
| 2004/0261177 | A1 | * | 12/2004 | Hoth et al. ................. 5/601 |
| 2005/0204472 | A1 | * | 9/2005 | Gagneur et al. ............ 5/601 |
| 2007/0143921 | A1 | * | 6/2007 | Hiyama ...................... 5/601 |
| 2007/0226906 | A1 | * | 10/2007 | Farooqui .................... 5/601 |
| 2008/0060133 | A1 | * | 3/2008 | Farooqui .................... 5/601 |
| 2008/0235874 | A1 | * | 10/2008 | Grosshauser et al. ..... 5/601 |
| 2009/0172882 | A1 | * | 7/2009 | Farooqui .................... 5/601 |

FOREIGN PATENT DOCUMENTS

| DE | 100 57 619 A1 | 5/2002 |
| DE | 103 25 302 B3 | 2/2005 |
| WO | 03037182 A1 | 5/2003 |

\* cited by examiner

Primary Examiner—Robert G Santos

(57) ABSTRACT

A module of a support apparatus (5) of a medical examination and treatment device, in particular of a magnetic resonance device (3), comprises the following features:
  a base unit (52) and a support unit (54) to support an examination object (1), which can travel in the horizontal direction in respect of the base unit (52), and
  a bracket unit (70) acting between the base unit (52) and the support unit (54), it being possible to move said bracket unit (70) against the base unit (52) and the support unit (54) and with which the support unit (54) can travel beyond the base unit (52).

28 Claims, 6 Drawing Sheets

SUPPORT DEVICE AND MAGNETIC RESONANCE DEVICE HAVING A SUPPORT DEVICE

CROSS REFERENCE TO RELATED APPLICATIONS

This application claims priority to the German applications No. 10357067.5, filed Dec. 4, 2003 and No. 10 2004 052 265.0, filed Oct. 27, 2004, which are incorporated by reference herein in their entirety.

FIELD OF INVENTION

The invention relates to a support apparatus for a medical examination and treatment device and a magnetic resonance device with a support apparatus of this type.

BACKGROUND OF INVENTION

In an imaging medical diagnostic device, for example a magnetic resonance device, a movable support apparatus of the device for an examination object, for example for a patient, is used to support the patient and to introduce him into an imaging volume of the device. Convenient embodiments of the support apparatus are designed to be height-adjustable, enabling the patient to mount the support apparatus at a low height, which is particularly advantageous when the patient is being moved out of a wheelchair. Once the patient has mounted and is supported, the support apparatus is raised by a motor into a vertical final position, from which a table top of the support apparatus, on which the patient lies, travels into the device by means of a horizontal movement. In one embodiment the table top slides in a guide frame of the support apparatus and is supported on a guide apparatus fitted in the examination space of the device, for example on rails of an interior paneling of the magnetic resonance device. The feed function of the horizontal movement is here provided by a drive which acts directly on the table top within the guide frame. In the arrangement described above the table top can be withdrawn from the guide frame as far as safe frictional connection of the drive unit to the table top can be ensured.

SUMMARY OF INVENTION

Providing the table top has sufficient inherent stability, the table top can extend at an opening of the examination space opposite the one from which the table top is introduced, so that a tilting moment of the table top can still be safely supported in the guide frame.

Until now a construction of a magnetic resonance device essentially shaped like a hollow cylinder has represented a compromise as regards its longitudinal extension and an imageable length of a patient lying once on the support apparatus between as good access as possible to the examination space, as little longitudinal extension as possible of the device, as large as possible an imaging volume and the associated costs. Typically the aforementioned devices are up to 1.6 m in length with a diameter of a cylindrical imaging volume of approximately 0.4 m. If in these circumstances a patient lying once on the support apparatus is to be imaged along his whole length of approximately 2 m, the minimum length of the table top is 2.7 m, whereby it is assumed that one end of the table top must remain 0.1 m in the guide frame of the support apparatus.

On the other hand the length of the table top conditioned by the anatomy of the patient is merely in a range of approximately 2.2 m. When using a 2.7 m long table top compared to a 2.2 m long table top, the installation space for the magnetic resonance device is larger, which needs to be provided for on the construction side and in particular represents a significant cost factor as a result of the larger HF shielding cabinet.

In addition a 2.7 m long table top in an embodiment in which the table top can be removed from the support apparatus and for example can be transferred to a trolley which can be connected to the support apparatus would considerable impair maneuverability of the decoupled trolley as well as the transportation of the patient in the hospital. For the above reasons only table tops with a length of approximately 2.2 m have therefore been used to date and the disadvantage that when a patient lies once thereon the imaging cannot cover the entire length of his body has been accepted.

DE 203 04 630 U1 discloses a couch with an extendible table top. The table top is height-adjustable and can be introduced into an examination device. The table top is designed to be significantly longer than a normal person. This produces the disadvantages already explained in that the examination device requires a larger installation space.

One object of the invention is thus to create an improved support apparatus of a magnetic resonance device, so that with a short table top the patient can be imaged along his entire length when he is lying once thereon.

This object is achieved by the claims. Advantageous embodiments are described in the dependent claims.

According to an embodiment of the invention, a module of a support apparatus, for example of a magnetic resonance device, has the following characteristics:

a base unit and a support unit for an examination object, which can travel in the horizontal direction in relation to the base unit, and a bracket unit acting between the base unit and the support unit, which can be moved in respect of the base unit and the support unit and with which the support unit can travel beyond the base unit.

Travel beyond the base unit means that, for example, the support unit leaves a horizontal extension of a guide apparatus in the base unit. The drive and a restricted guidance is achieved with the bracket unit. By means of a module in accordance with the invention an advantageously short support unit allows the whole length of a patient lying once on the support unit, to be introduced into a capture area of the imaging examination device and to be imaged accordingly. In this case the bracket unit spans the distance between the end of the support unit and the guide apparatus of the base unit. Medical examination and treatment devices which can have a support apparatus according to the invention are—besides the aforementioned imaging examination device for magnetic resonance tomography—computer tomography and ultrasound devices, and radiotherapy devices.

BRIEF DESCRIPTION OF THE DRAWINGS

Further advantages, characteristics and details of the invention emerge from the exemplary embodiments of the invention described below on the basis of FIGS. 1 to 8, in which.

DETAILED DESCRIPTION OF INVENTION

To summarize, the disadvantages mentioned in the introduction which are associated with a longer table top can be avoided if a support apparatus according to the invention is used to image the entire length of the body. This is achieved in that a table top essentially leaves a base unit. A support apparatus according to the invention has for example the following structure:

The base unit comprises:
  a motor to drive the transverse movement of the table top into and out of the target area defined by the examination or treatment device,
  guide rails which enable the table top to be held and moved tilt-free, as long as the table top can still at least partially be held by the base unit and
  if necessary a vertical lifting device, to raise and lower the table top.

The support unit comprises:
  the table top,
  a gear rack arranged on the underside of the table top and
  a pressure device for contact holding of the gear rack with a bracket toothed belt of a bracket unit.

The bracket unit with a drive-side and an output-side end comprises:
  a telescopic bracket which connects the drive-side and the output-side end to one another and allows the table top to move beyond the base unit,
  a slide arranged on the drive side, which can be moved in respect of the base unit via drive belts driven by the motor and
  a differential gear integrated into the slides, which converts the movement of the drive belt on the one hand into a first translation movement of the slide and thus of the support unit and on the other hand drives the bracket toothed belt, which has teeth on both sides, engages on the output side into the gear rack and effects a second translation movement of the support unit.

In the following this exemplary design is clarified on the basis of the figures.

Figure 1:
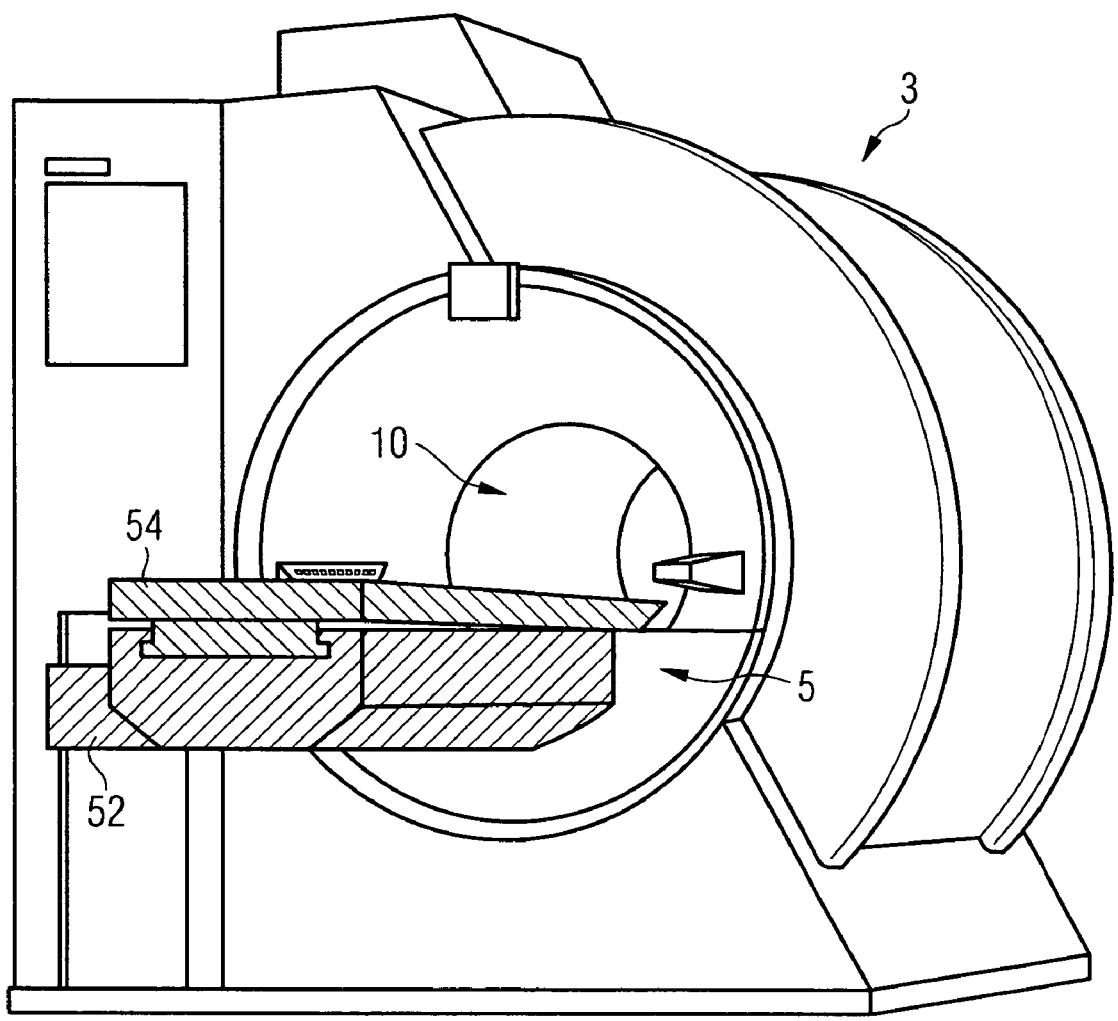
FIG. 1 shows a perspective view of a magnetic resonance device with a tunnel-shaped patient capture space and with a support apparatus, containing a module which can travel in the vertical direction with a support unit which can travel in the horizontal direction and a base unit.

FIG. 1 shows a perspective view of a magnetic resonance device with a tunnel-shaped patient capture space 10. In order to introduce an area to be imaged of a patient 1 into an imaging volume 15 of the magnetic resonance device within the patient capture space 10, the magnetic resonance device comprises a support apparatus 5, the height-adjustable module of which is indicated by hatching. The module here comprises a support unit 54 that can travel in the horizontal direction and a corresponding base unit 52 inter alia for driving and guiding the support unit 54. FIG. 1 shows the support unit 54 partially withdrawn into the patient capture space 10.

Figure 2:
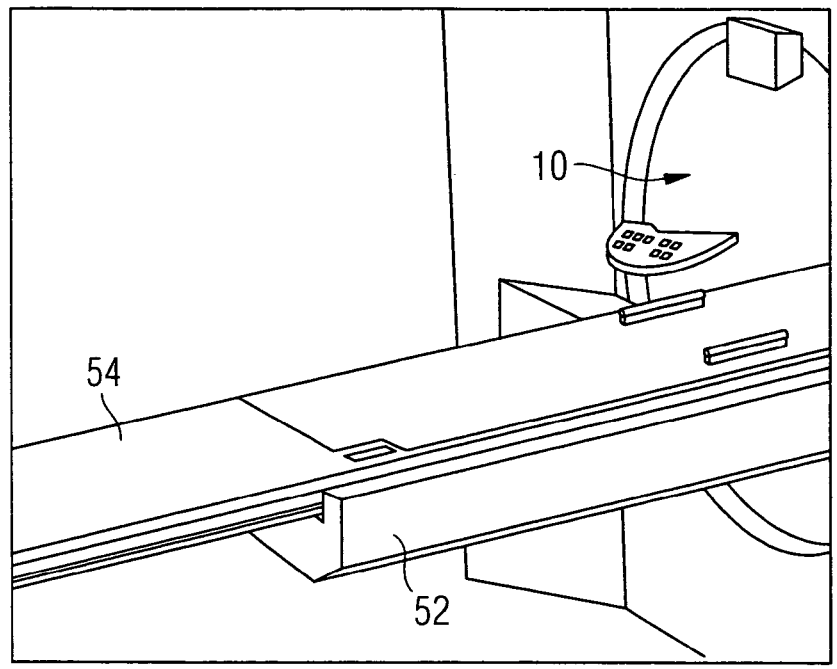
FIG. 2 shows, as a section of FIG. 1 in perspective view, the module, whereby compared to FIG. 1 the support unit is shown fully extended out of the patient capture space, FIG. 3 likewise shows, as a section of FIG. 1 in perspective view, the module, whereby compared to FIG. 1 the support unit is shown fully extended out of the patient capture space, a patient is lying on the support unit and a local high-frequency antenna is mounted on the support unit.

FIG. 2 shows, as a section of FIG. 1 likewise in perspective view, the module, whereby in FIG. 2 the support unit 54 is shown fully extended out of the patient capture space 10 in contrast to FIG. 1. In this fully extended state of the support unit 54 the module can be lowered in order to enable the patient 1 for example to mount the support unit 54 with ease.

Figure 3:
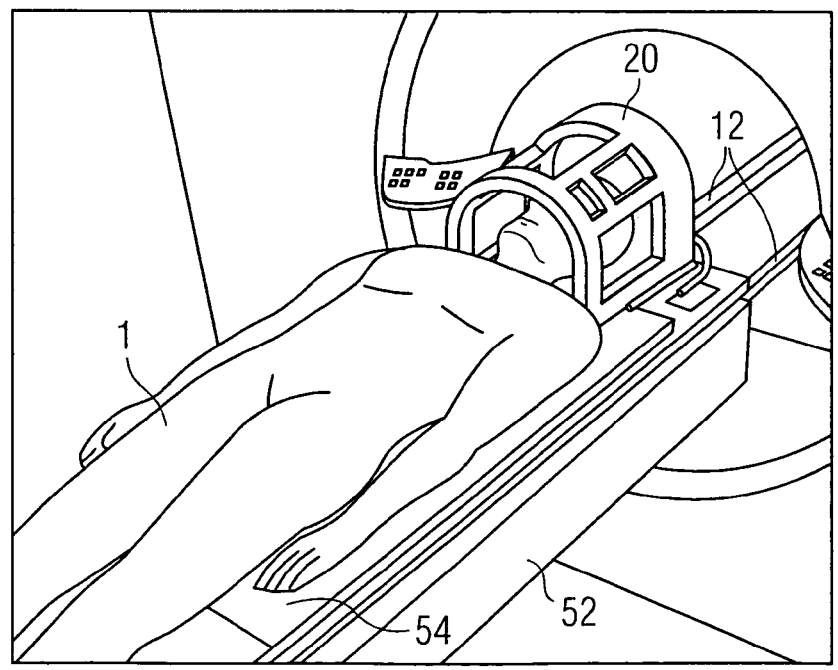

FIG. 3 likewise shows, as a section of FIG. 1 in perspective view, the module, whereby in contrast to FIG. 1 the support unit 54 is fully extended out of the patient capture space 10, the patient is lying on the support unit 54 and a local high-frequency antenna 20 for head scans is mounted on the support unit 54 to examine the head of the patient 1. As can be seen from FIG. 3, a rail-type guide apparatus 12 in the patient capture space 10 is designed to guide and support the support unit 54 within the patient capture space 10.

To prevent the support unit 54 from tilting when extended, guide rollers can for example be arranged above the guide apparatus 12 on the side facing the base unit 52. This holds the support unit 54 so that it cannot tilt, for example even after leaving clamping guide rails arranged in the base unit 52 when the end of the support unit 54 remote from the base unit 52 is loaded.

Figure 4:
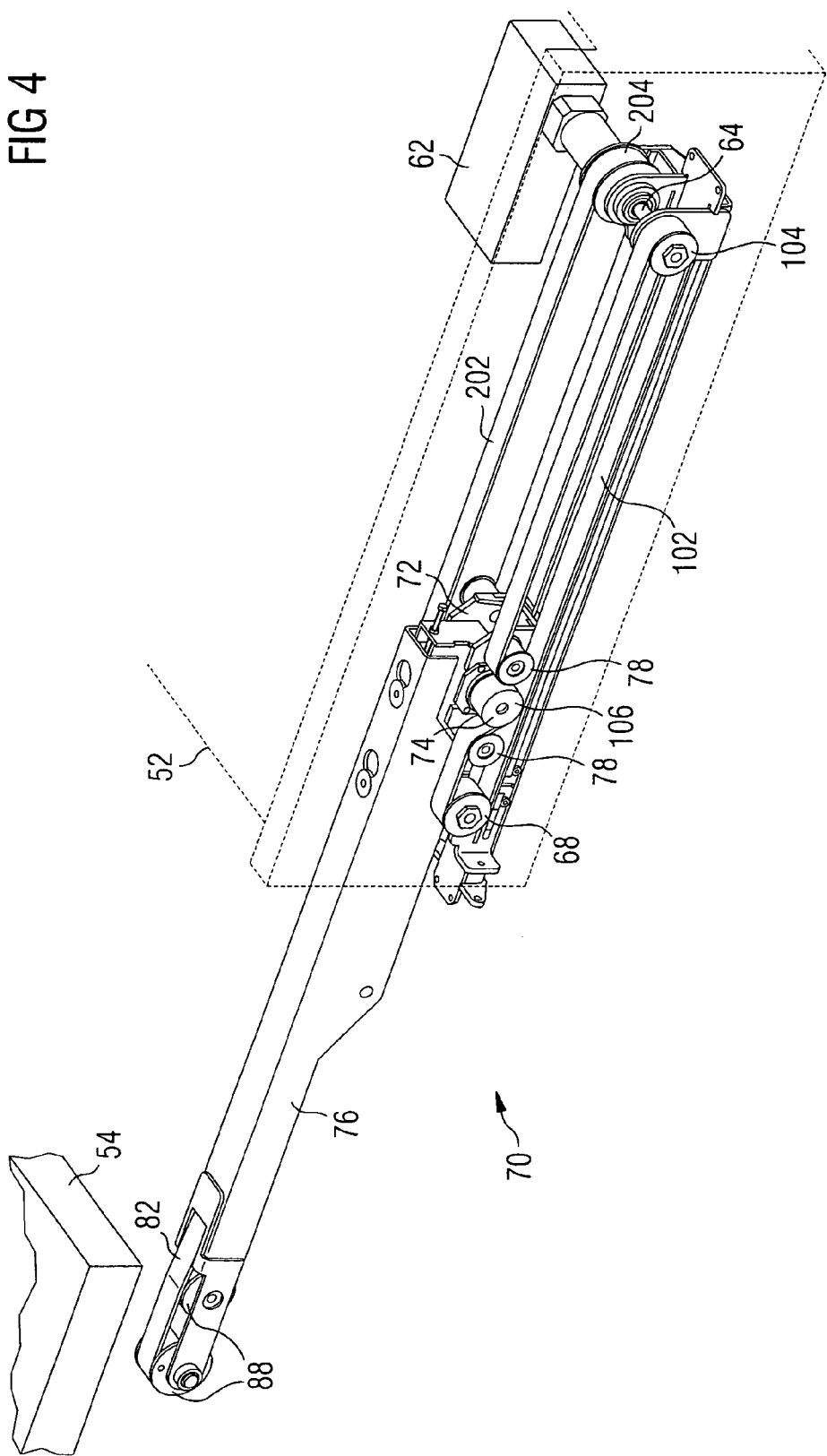
FIGS. 4 and 5 show in perspective view essentially a bracket unit of the module which can travel in the horizontal direction, by means of which the support unit can travel beyond a horizontal extension of the base unit.
Figure 5:
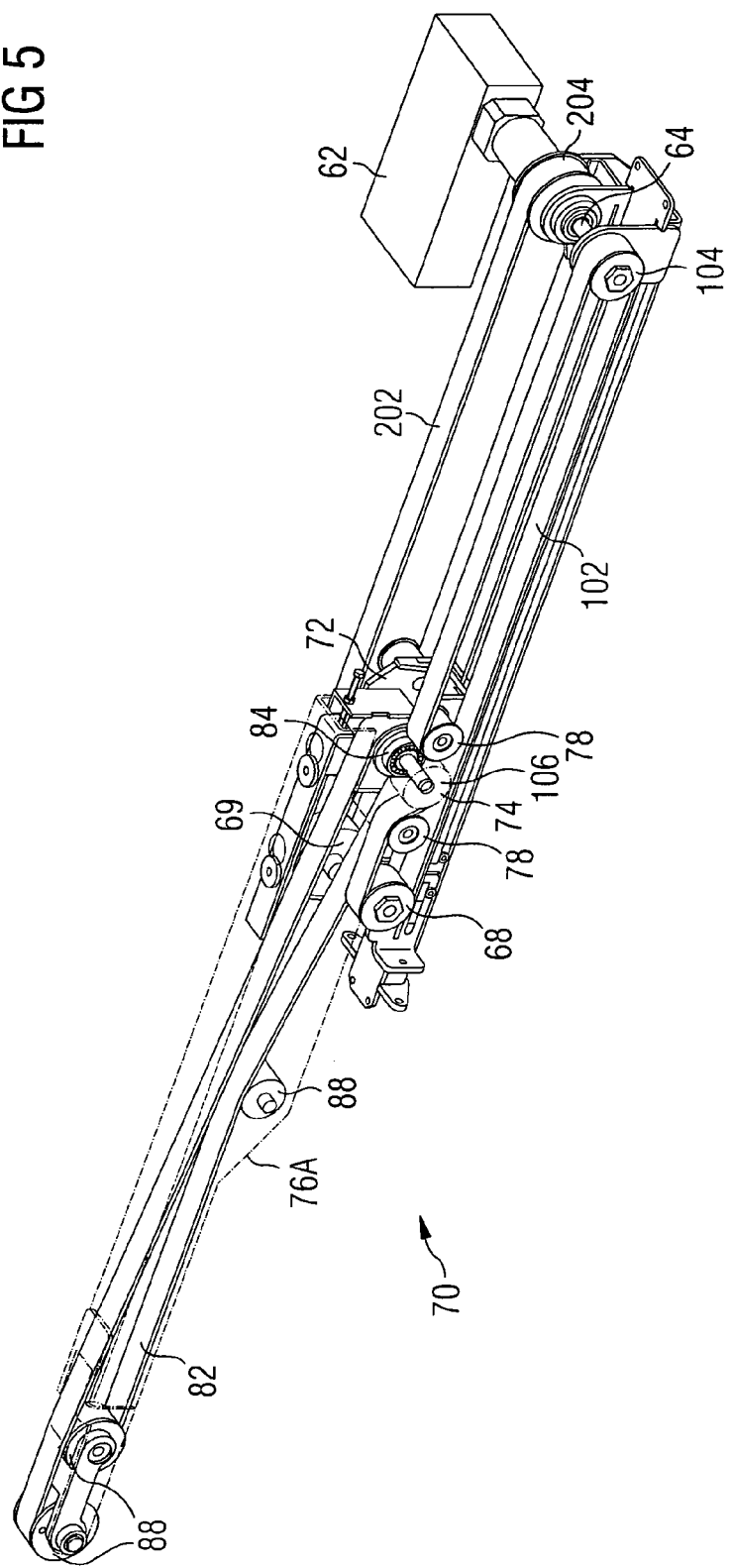

FIGS. 4 and 5 show as an exemplary embodiment of the invention in perspective view a bracket unit which can travel in the horizontal direction, by means of which the support unit 54 can travel beyond a horizontal extension of the base unit 52. FIG. 4 is kept as a traditional design drawing here, in contrast to which in FIG. 5 a bracket 76 of the bracket unit is represented only by a side wall 76A for a better understanding of the method of functioning.

The base unit 52 contains a drive for moving the support unit 54. This on the one hand effects a movement of the bracket unit 70, which correlates with a movement of the support unit 54 connected to it, and on the other hand drives a drive unit of the bracket unit 70, which for its part effects a further movement of the support unit 54 in respect of the bracket unit 70.

These two movement mechanisms can be driven with a single motor 62 arranged within the base unit 52 and fastened to it. The motor 62 has a motor shaft 64, to which a first drive gear wheel 104 for a first toothed belt 102 and a second drive gear wheel 204 for a second toothed belt 202 are attached. Thus in this embodiment a single motor 62 advantageously effects a simultaneous movement of the bracket un it 70 in respect of the base unit 52 and of the support unit 54 in respect of the bracket unit 70. In view of its effect on for example a magnetic field of the magnetic resonance device it is thus advantageous to compensate only the one motor 62. Furthermore, two deflection gear wheels 68 and 69 mounted so as to rotate in respect of the base unit 52 and associated with the drive are provided to guide the toothed belts 102 and 202.

In the following, the movement of the bracket unit 70 in respect of the base unit 52 is first discussed and then the movement of the support unit 54 in respect of the bracket unit 70.

The bracket unit 70 comprises a slide 72 which can travel horizontally within the base unit 52, the bracket 76 being attached to said slide 72. Travel of the slide 72 is effected by the two toothed belts 102 and 202. To this end a slide shaft 74 is mounted in the slide 72, on which a first conversion gear wheel 106 is attached, on which the first toothed belt 102 acts and to which a second conversion gear wheel 206 is attached, on which the second toothed belt 202 acts. Furthermore the bracket unit comprises several rotatably mounted pressure gear wheels 78 to guide the toothed belts 102 and 202. If the two toothed belts 102 and 202 act in counter-rotation on the slide shaft 74 and effect in whatever manner (different sizes of gear wheels, different tooth pitch) rotations of different strengths, the slide moves transversely, in order to equalize the different speeds of rotation.

Figure 6:
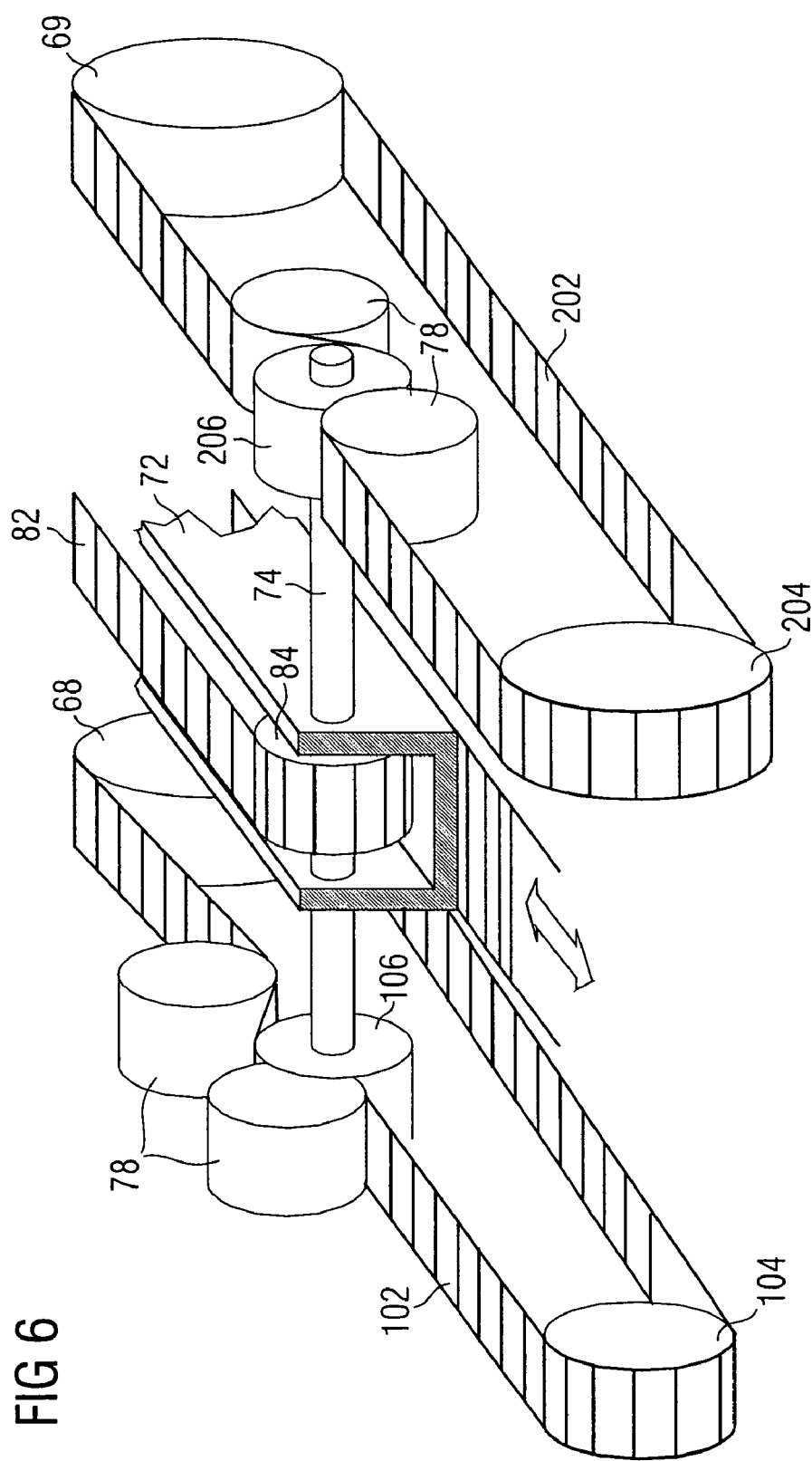
FIG. 6 shows, as a section of FIGS. 4 and 5 in schematically simplified form, a slide of the bracket unit and a drive unit for the bracket unit.

FIG. 6 to this end shows as a section of FIGS. 4 and 5 in schematically simplified manner the slide 72 with the gear wheels 106, 206 and 78 as well as parts of the drive with the gear wheels 104, 204, 68 and 69 and the toothed belts 102 and 202.

If the two conversion gear wheels 106 and 206 were identical and the two toothed belts 102 and 202 had an identical speed, the slide 72 would not move. Travel of the slide 72 is achieved by one or more of the measures described below:

the two drive gear wheels 104 and 204 are designed in particular in respect of their size such that they effect a different speed of the toothed belts 102 and 202, the two conversion gear wheels 106 and 206 are designed differently, particularly in respect of their size, the two toothed belts 102 and 202 have a different tooth pitch, at least one of the toothed belts 102 and 202 has a different tooth pitch on the front and rear sides.

With identical conversion gear wheels 106 and 206 the speed of the slide 72 is half a differential speed of the two toothed belts 102 and 202.

A movement of the support unit 54 in respect of the bracket unit 70 is achieved as follows. A further drive gear wheel 84 is attached to the slide shaft 74, and via a further toothed belt 82 transfers the rotational movement of the slide shaft 74 to an end of the bracket 76 opposite the slide 72. The toothed belt 82 is diverted in the bracket 76 by means of the diversion gear wheels 88. The toothed belt 82 has a tooth pitch on both sides. At the end of the bracket 76 the toothed belt 82 ensures that the rotational movement is converted into a travel movement of the support unit 54. To this end the toothed belt 82 engages, with the tooth pitch lying on its outer side, into a gear rack, which for example is arranged on an underside of the support unit 54. A pressure apparatus holds, for example, gear rack and toothed belt 82 together.

The embodiment described above in this way enables the support unit 54 to travel beyond a horizontal extension of the base unit 52, whereby the bracket unit spans the distance between the end of the support unit 54 and of a guide frame of the base unit 52 and taps the necessary energy to move the support unit 54 from the motor 62 and feeds it to the two movement mechanisms. This enables whole-body imaging of the patient 1 lying once on the support unit 54, inter alia with a comparatively short support unit 54.

Figure 7:
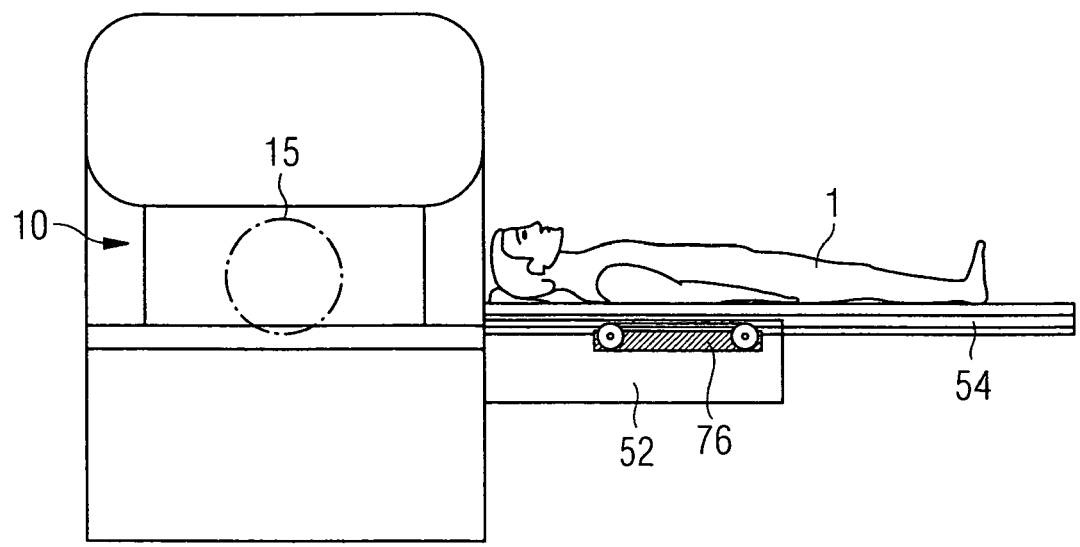
FIG. 7 shows, as a fundamental sectional view of the magnetic resonance device, a position of the bracket unit when the support unit is maximally extended out of the patient capture space
Figure 8:
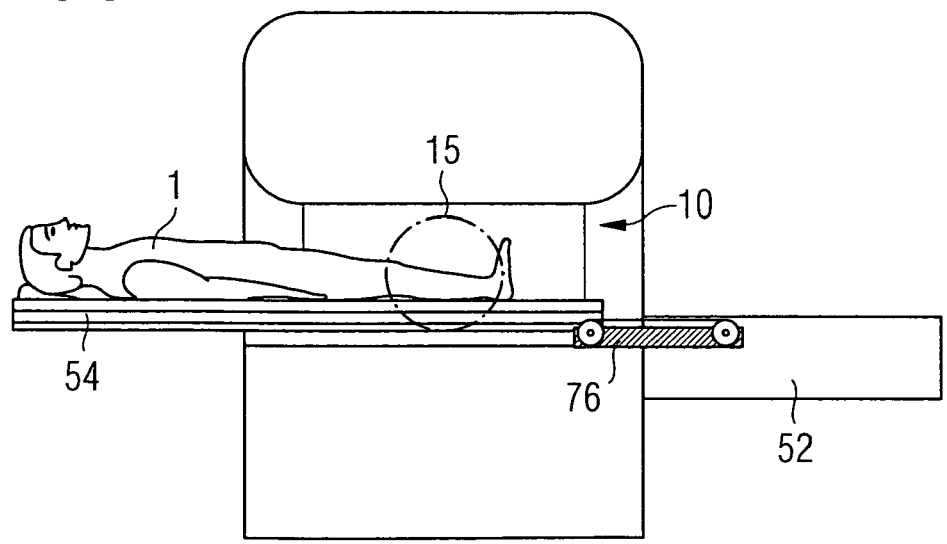
FIG. 8 shows, as a fundamental sectional view of the magnetic resonance device, a position of the bracket unit when the support unit is maximally withdrawn into the patient capture space.

The further drive gear wheel 84 and/or the further toothed belt 82 are designed here such that the bracket unit, when the support unit 54 is maximally introduced into the patient capture space 10, is sufficiently adjusted and on the other hand when the support unit 54 is fully extended out of the patient capture space 10 the bracket unit is fully withdrawn in the base unit 52, thus enabling the module to be lowered. FIG. 7 shows to this end, as a fundamental sectional drawing, the position of the bracket unit 70 when the support unit 54 is maximally extended out of the patient capture space 10 and FIG. 8 shows the position of the bracket unit 70 when the support unit 54 is maximally introduced into the patient capture space 10.

In one embodiment the rail-type guide apparatus 12 is designed within the patient capture space 10 to be connected to the support unit 54, for example by the previously mentioned use of rollers arranged above the guide apparatus 12, such that the support unit 54 is secured against tilting around a horizontal axis perpendicular to the direction of travel. As a result the bracket unit 70 must in principle only transfer the drive energy for travel of the support unit 54 and need not take up any retention forces against said tipping of the support unit 54, so that the bracket unit 70, in particular the parts thereof which can travel into the patient capture space 10, can easily be realized by highly magnetic-resonance-compatible components made of plastic.

In another embodiment, in order to prevent said tilting, the rail-type guide apparatus 12 is simply extended beyond the patient capture space 10. In yet another embodiment said retention forces against said tilting are produced by the bracket unit, whereby it is designed to be correspondingly load-bearing while retaining magnetic resonance compatibility.

The invention claimed is:

1. A support device for a medical examination and treatment device, comprising:

a base unit;

a support unit for supporting an examination object, the support unit adapted to travel in a horizontal direction relative to the base unit; and a cantilever arm functionally arranged between the base unit and the support unit, the cantilever arm movable relative to the base and the support units, wherein the support unit is adapted to travel beyond the base unit using the cantilever arm, wherein the cantilever arm has a sliding carriage movable within the base unit, the sliding carriage comprising:

a carriage shaft having a first toothed wheel operatively connected to a first toothed belt and a second toothed wheel operatively connected to a second toothed belt; and a guiding unit for guiding the first and second toothed belts such that the first and second toothed belts effect a counter-rotation of the carriage shaft relative to a rotational direction of the first and second toothed belts.

2. The support device according to claim 1, wherein the base unit comprises:

a first toothed belt transmission unit including a first drive gear wheel and the first toothed belt;

a second toothed belt transmission unit including a second drive gear wheel and the second toothed belt.

3. The support device according to claim 1, wherein the slide carriage is movable using the first and second drive gear wheels, the first and second drive gear wheels adapted to effect a first speed of the first toothed belt and a second speed of the second toothed belt, wherein the first speed is different from the second speed.

4. The support device according to claim 3, wherein the first drive gear wheel has a different size than the second drive gear wheel.

5. The support device according to claim 1, wherein the slide carriage is movable using the first and second toothed wheels of the carriage shaft, the first and second toothed wheels having different sizes.

6. The support device according to claim 1, wherein the slide carriage is movable using the first and second toothed belts, the first and second toothed belts having different tooth pitches.

7. The support device according to claim 1, wherein the slide carriage is movable using the first and second toothed belts, at least one of the toothed belts having a first tooth pitch arranged on a front side of the respective toothed belt which is different from a second tooth pitch arranged on a rear side of the respective belt.

8. The support device according to claim 1, wherein the slide carriage comprises an arm and the carriage shaft comprises a third drive gear wheel for guiding a third toothed belt, the third toothed belt adapted to move the support unit relative to the cantilever arm by transmitting an operating power of the carriage shaft to an end of the arm, the end of the arm located opposite the slide carriage.

9. The support device according to claim 1, wherein
the medical examination and treatment device is a medical imaging examination device;
the support unit is adapted to travel into an examination object accommodating area of the medical imaging examination device; and
a boundary of the examination object accommodating area has a guiding track for guiding the support unit.

10. The support device according to claim 9, wherein the guiding track is adapted to prevent the support unit from tilting.

11. The support device according to claim 10, wherein the support unit is prevented from tilting relative to a horizontal axis perpendicular to a direction of travel of the support unit.

12. The support device according to claim 1, wherein the support device is adapted to travel in a vertical direction relative to a supporting apparatus having the supporting device.

13. A support device for a medical examination and treatment device, comprising:
a base unit;
a support unit for supporting an examination object, the support unit adapted to travel in a horizontal direction relative to the base unit; and
a cantilever arm functionally arranged between the base unit and the support unit, the cantilever arm movable relative to the base and the support units, wherein the support unit is adapted to travel beyond the base unit using the cantilever arm,
wherein the base unit includes a motor adapted to move the cantilever arm relative to the base unit and to move the support unit relative to the cantilever arm, both movements carried out in parallel by the motor, and
wherein the cantilever arm has a sliding carriage movable within the base unit, the sliding carriage comprising:
a carriage shaft having a first toothed wheel operatively connected to a first toothed belt and a second toothed wheel operatively connected to a second toothed belt; and
a guiding unit for guiding the first and second toothed belts such that the first and second toothed belts effect a counter-rotation of the carriage shaft relative to a rotational direction of the first and second toothed belts.

14. The support device according to claim 13, wherein the base unit comprises:
a first toothed belt transmission unit including a first drive gear wheel and the first toothed belt;
a second toothed belt transmission unit including a second drive gear wheel and the second toothed belt, wherein the first and second toothed belt transmission units are driven by the motor.

15. The support device according to claim 14, wherein the first and second drive gear wheels are arranged on a common drive shaft of the motor.

16. A magnetic resonance device, comprising a support device, the support device comprising:
a base unit;
a support unit for supporting an examination object, the support unit adapted to travel in a horizontal direction relative to the base unit; and
a cantilever arm functionally arranged between the base unit and the support unit, the cantilever arm movable relative to the base and the support units, wherein the support unit is adapted to travel beyond the base unit using the cantilever arm,
wherein the cantilever arm has a sliding carriage movable within the base unit, the sliding carriage comprising:
a carriage shaft having a first toothed wheel operatively connected to a first toothed belt and a second toothed wheel operatively connected to a second toothed belt; and
a guiding unit for guiding the first and second toothed belts such that the first and second toothed belts effect a counter-rotation of the carriage shaft relative to a rotational direction of the first and second toothed belts.

17. The magnetic resonance device according to claim 16, wherein the base unit includes a motor adapted to move the cantilever arm relative to the base unit and to move the support unit relative to the cantilever arm, both movements carried out in parallel by the motor.

18. The magnetic resonance device according to claim 16, wherein the base unit comprises:
a first toothed belt transmission unit including a first drive gear wheel and the first toothed belt;
a second toothed belt transmission unit including a second drive gear wheel and the second toothed belt.

19. The magnetic resonance device according to claim 18, wherein the first and second drive gear wheels are arranged on a common drive shaft of a motor adapted to move the cantilever arm relative to the base unit and to move the support unit relative to the cantilever arm, both movements carried out in parallel by the motor.

20. The magnetic resonance device according to claim 16, wherein the slide carriage is movable using the first and second drive gear wheels, the first and second drive gear wheels adapted to effect a first speed of the first toothed belt and a second speed of the second toothed belt, wherein the first speed is different from the second speed.

21. The magnetic resonance device according to claim 16, wherein the slide carriage is movable using the first and second toothed wheels of the carriage shaft, the first and second toothed wheels having different sizes.

22. The magnetic resonance device according to claim 16, wherein the slide carriage is movable using the first and second toothed belts, the first and second toothed belts having different tooth pitches.

23. The magnetic resonance device according to claim 16, wherein the slide carriage is movable using the first and second toothed belts, at least one of the toothed belts having a first tooth pitch arranged on a front side of the respective toothed belt which is different from a second tooth pitch arranged on a rear side of the respective belt.

24. The magnetic resonance device according to claim 16, wherein the slide carriage comprises an arm and the carriage shaft comprises a third drive gear wheel for guiding a third toothed belt, the third toothed belt adapted to move the support unit relative to the cantilever arm by transmitting an operating power of the carriage shaft to an end of the arm, the end of the arm located opposite the slide carriage.

25. The magnetic resonance device according to claim 16, the medical examination and treatment device is a medical imaging examination device;

the support unit is adapted to travel into an examination object accommodating area of the medical imaging examination device; and a boundary of the examination object accommodating area has a guiding track for guiding the support unit.

26. The magnetic resonance device according to claim 25, wherein the guiding track is adapted to prevent the support unit from tilting.

27. The magnetic resonance device according to claim 26, wherein the support unit is prevented from tilting relative to a horizontal axis perpendicular to a direction of travel of the support unit.

28. The magnetic resonance device according to claim 16, wherein the support device is adapted to travel in a vertical direction relative to a supporting apparatus having the supporting device.

* * * * *

UNITED STATES PATENT AND TRADEMARK OFFICE
CERTIFICATE OF CORRECTION

PATENT NO. : 7,634,827 B2
APPLICATION NO. : 11/001603
DATED : December 22, 2009
INVENTOR(S) : Gagneur et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1300 days.

Signed and Sealed this

Ninth Day of November, 2010

David J. Kappos
*Director of the United States Patent and Trademark Office*